US00PP35302P2

(12) United States Plant Patent
Slaughter et al.

(10) Patent No.: US PP35,302 P2
(45) Date of Patent: Aug. 8, 2023

(54) PEACH TREE NAMED 'WAPEACHTHREE'

(50) Latin Name: *Prunus persica*
Varietal Denomination: Wapeachthree

(71) Applicant: Wawona Packing Co., LLC, Cutler, CA (US)

(72) Inventors: John Keith Slaughter, Fresno, CA (US); Kaylan M. Roberts, Fresno, CA (US)

(73) Assignee: Wawona Packing Co., LLC, Cutler, CA (US)

( * ) Notice: Subject to any disclaimer, the term of this patent is extended or adjusted under 35 U.S.C. 154(b) by 0 days.

(21) Appl. No.: 17/803,823

(22) Filed: Dec. 9, 2022

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./197
CPC ... A01H 5/08; A01H 5/00; A01H 6/74; A01H 6/7463
See application file for complete search history.

(56) References Cited

U.S. PATENT DOCUMENTS

PP15,496 P2 * 1/2005 Slaughter ..... A01H 5/08 Plt./197

* cited by examiner

*Primary Examiner* — June Hwu
(74) *Attorney, Agent, or Firm* — Potter Anderson & Corroon LLP

(57) ABSTRACT

A new and distinct variety of peach tree (*Prunus persica*), which is denominated varietally as 'Wapeachthree', and which produces an attractively colored yellow-fleshed, clingstone peach which is mature for harvesting and shipment approximately October 25 to November 1 under the ecological conditions prevailing in the San Joaquin Valley of central California.

1 Drawing Sheet

Botanical designation: *Prunus persica.*
Varietal denomination: 'Wapeachthree'.

BACKGROUND OF THE NEW VARIETY

The present variety of peach tree resulted from an ongoing program of fruit tree and rootstock breeding. The purpose of this program is to improve the commercial quality of deciduous fruit varieties and rootstocks by creating and releasing promising selections of *Prunus* species. To this end, both controlled and hybrid cross pollinations are made each year to produce seedling populations from which improved progenies are evaluated and selected.

The seedling 'Wapeachthree' was originated by the breeders and selected from a population of seedlings growing experimental orchards located near Fowler, Calif. The seedlings, grown on their own roots, were derived from planting seed of a seedling designated as 'P4.097'. This maternal parent, which provided the seed of the current variety, was not a controlled cross, but was the result from an open pollination or just as likely self-pollination. The resulting fruit was collected from the female parent at a mature stage and seeds were extracted in August of 2009. After a period of stratification, the seed was placed in the greenhouse by population and then field planted for tree establishment, and ultimately to exhibit fruit for evaluation. One yellow-fleshed peach seedling, which is the present variety, exhibited especially desirable characteristics and was then designated as 'V1.313'. This seedling was marked for subsequent observation. After the 2013 fruiting season, the new variety of peach tree was selected for advanced evaluation and repropagation.

ASEXUAL REPRODUCTION

Asexual reproduction of this new and distinct variety of peach tree was accomplished by budding the new peach tree onto 30 trees of 'Nemaguard' Rootstock (un-patented). This was performed at an experimental orchard located near Fowler, Calif. Subsequent evaluations of these asexually reproduced plants have shown those asexual reproductions run true to the original tree. All characteristics of the original tree and its fruit were established and appear to be transmitted through these succeeding asexual propagations.

SUMMARY OF VARIETY

'Wapeachthree' is a new and distinct variety of peach tree, which is considered of relatively large size, and which has a vigorous growth characteristic. This new tree is also a regular and productive bearer of relatively large, firm, yellow-fleshed, clingstone fruit which have a very good flavor and eating qualities.

This new peach tree has a medium chilling requirement of approximately 600 hours, and further produces relatively uniformly sized fruit throughout the tree's canopy. In addition to the foregoing, the fruit of the new peach also appears to have good handling and shipping qualities. The 'Wapeachthree' peach tree bears fruit which are typically ripe for commercial harvesting and shipment on approximately October 25 to November 1 under the ecological conditions prevailing in the San Joaquin Valley of central California. In relative comparison to the 'Calara' peach tree (U.S. Plant Pat. No. 15,496), which is the closest known variety, the current variety of peach tree bears fruit that ripens approximately 20 days later than the comparator variety. 'Wapeachthree' peach tree was selected from a seedling population of the 'P4.097' (an unpatented peach selection). This population was the result of planting open pollenated seed of the fruit from the 'P4.097' selection, which means that the seed and pollen parent are most likely the same. In that case there are two major distinctions that separate the 'Wapeachthree' peach tree and the 'P4.097' (seed parent, and assumed pollen parent) which is that 'Wapeachthree' produces clingstone fruit while the parent variety produces freestone and 'Wapeachthree' bears fruit that ripens more than 24 days later than the parents variety.

BRIEF DESCRIPTION OF THE DRAWING

FIG. 1 is a color photograph of two whole mature fruit harvested from a fifth leaf year tree displaying both the apical and basal fruit aspects. One mature fruit is bisected transversely through the sutural plane to reveal the flesh color and stone characteristics. Additionally, a wedge of fruit is included and reveals flesh coloration. The external coloration of the fruit as shown in the photograph is sufficiently matured for harvesting and shipment. Additionally, one of the bisected fruit hemispheres displays a typical stone still in contact with fruit but with the flesh removed. The colors in these photographs are as nearly true as is reasonably possible in a color representation of this type. Due to chemical development, processing. and printing, the fruit depicted in this photograph may, or may not, be accurate when compared to the actual specimen. For this reason, future color references should be made to the color plates (Royal Horticultural Society, Fourth Edition, 2001) and descriptions provided herein.

NOT A COMMERCIAL WARRANTY

The following detailed description has been prepared to solely comply with the provisions of 35 U.S.C. § 112 and does not constitute a commercial warranty (either expressed or implied) that the present variety will in the future display all the botanical, pomological, or other characteristics as set forth, hereinafter. Therefore, this disclosure may not be relied upon to support any future legal claims including, but not limited to, breach of warranty of merchantability, fitness for any purpose, or non-infringement which is directed, in whole, or in part, to the present variety.

DETAILED DESCRIPTION

Referring more specifically to the pomological details of this new and distinct variety of peach tree. the following has been observed during the seventh fruiting season and under the ecological conditions prevailing at the orchards of the assignee which are located near the town of Fowler, county of Fresno, state of California. All major color code designations are by reference to The R.H.S. Colour Chart (Royal Horticultural Society, Fourth Edition, 2001) provided by The Royal Horticultural Society of Great Britain. Common color names are also occasionally used.

Tree:

*Size*.—Generally considered medium to medium-large in its growth pattern as compared to other common commercial peach cultivars ripening in the late season of maturity. The tree of the present variety was pruned to a height of about 270.0 cm to about 310.0 cm at commercial maturity. Fruit size can vary with crop load and the conditions under which the fruit and tree are grown.

*Width*.—About 275.0 cm.

*Vigor*.—Considered moderately vigorous. The present peach tree variety grew from about 180.0 cm to about 185.0 cm in height during the second growing season. The new variety was pruned to a height of about 150.0 cm during the first dormant season, and primary scaffolds were then selected for the desired tree structure.

*Productivity*.—Productive. Fruit set varies from the desired crop load to levels higher than desired amounts when the new variety is grown in a suitable horticultural zone and under appropriate commercial nursery conditions. The fruit set is spaced by thinning to develop the remaining fruit into the desired market-sized fruit. The number of the fruit set varies with the prevailing climatic conditions and the cultural practices employed.

*Fruit bearing*.—Regular. Fruit set has been more than adequate during the previous years of observation, and thinning was necessary during the past 8 years on both the original seedling and on subsequent asexually reproduced trees.

*Tree form*.—Upright and pruned into a vase shape.

*Density*.—Considered moderately dense.

*Hardiness*.—The present tree was grown and evaluated in USDA Hardiness Zone 9. The calculated winter chilling requirements of the new tree is approximately 600 hours at a temperature below 7.0 degrees C. The present variety appears to be hardy under typical central San Joaquin Valley climatic conditions.

Trunk:

*Diameter*.—About 20.0 cm in diameter when measured at about 15.5 cm above the soil level. This measurement was taken at the beginning of the sixth growing season.

*Bark texture*.—Considered moderately rough with folds of papery scarfskin being present. Since bark development and coloration change with advancing tree age this characteristic varies with the tree vigor, age, and regional conditions. Therefore, this is not a dependable descriptor of the new variety.

*Lenticels*.—Numerous flat. oval lenticels are present. The lenticels range in size from about 2.5 mm to about 6.0 mm in width, and between about 1.0 mm and about 2.0 mm in height.

*Lenticel color*.—Considered an orange-brown (RHS Greyed-Orange Group 166 C).

*Bark coloration*.—Variable, but it is generally considered to be a greyed tan (RHS Greyed-Brown Group 177 A). This bark description was taken from trees in their seventh leaf which have ruptured the scarf skin, and which also have developed bark furrowing which is much more typical of the bark of older trees.

Branches:

*Size*.—Considered medium large for the variety.

*Diameter*.—Average as compared to other peach varieties. The branches have a diameter of about 13.5 cm when measured during the sixth year after grafting.

*Flowering shoot thickness*.—Average for the species. Generally, the most consistent flower bud development and therefore potential fruiting sites occur on shoots which are about 7.0 mm in at the time of bloom.

*Flowering shoot anthocyanin colorization*.—Characterized as very weak intensity.

*Surface texture*.—Average and appearing relatively smooth.

*Crotch angles*.—Primary branches are considered variable and are usually growing at an angle of about 50 degrees when measured from a horizontal plane.

*Current season shoots*.—Surface texture — Substantially glabrous.

*Internode length*.—About 2.7 cm.

*Color of mature branches*.—Approximately Grey brown (RHS Greyed-Orange Group 165 A).

*Current season's shoots*.—Color. — Light green (RHS Yellow-Green Group N144 A). The color of new shoot tips is considered a light green (RHS Yellow-Green Group 145 A). The vegetative shoot color can be significantly influenced by plant nutrition. irrigation practices. and exposure to sunlight, and therefore should not be considered a consistent botanical characteristic of this new variety.

Leaves:

*Size*.—Considered average for the species. Leaf measurements have been taken from vigorous, upright, current-season growth at approximately mid-shoot. The leaf size is often influenced by prevailing growing conditions, quality and intensity of available sunlight, and the location of the leaf within the tree canopy. For this reason, leaf sizes can vary significantly based upon the ambient light and other cultural factors listed above and are not typically considered a dependable botanical descriptor.

*Leaf length*.—About 145.0 mm to about 165.0 mm.

*Leaf width*.—About 33.0 mm to about 39.0 mm.

*Leaf base-shape*.—The leaves generally exhibit equal marginal symmetry relative to the leaf longitudinal axis.

*Leaf form*.—Lanceolate.

*Leaf tip form*.—Acuminate.

*Leaf color*.—Upper Leaf Surface — Medium green (approximately RHS Green Group 136 A).

*Leaf texture*.—Upper Leaf Surface — Glabrous. Lower Leaf Surface — Glabrous.

*Leaf color*.—Lower Leaf Surface — Medium yellow-green (approximately RHS Green Group N138 A).

*Leaf venation*.—Pinnately veined.

*Mid-vein*.—Color — Considered a pale green (approximately RHS Yellow- Green Group 145 D). There is no observed difference in color on the leaf surfaces.

*Leaf margins*.—Gently undulating. Form. — Considered crenulate. Uniformity. — Generally uniform.

*Leaf petioles*.—Form. — Considered canaliculated and having a more pronounced trough when viewed from the dorsal aspect. The petiole margin is considered rounded when viewed from the ventral aspect. Size. — Considered large for the species. Length. — About 10.0 mm to about 12.0 mm. Diameter. — About 1.5 mm to about 2.0 mm. Color. — A light green (approximately RHS Yellow-Green Group 145 C). Texture. — Glabrous. Strength. — Durable for species until senescence.

*Leaf glands*.—Size. — Considered relatively small for the species; about 1.7 mm in width, and about 1.5 mm in height. Number. — Generally. one per marginal side. Occasionally, two glands per side are found. Observations of more than two glands per marginal side are very uncommon. Type. — Glands located at the base of the leaf are predominantly reniform in shape. An additional one to two, or occasionally more glands, can be found in this variety. Color. — Considered a yellowed green (approximately RHS Yellow-Green Group 146 C).

*Leaf stipules*.—Size. — Medium large for this variety. Number. — Typically. 2 per leaf bud, and up to 6 per shoot tip. Form. — Lanceolate in form and having a serrated marginal edge. Color. — Green (approximately RHS Yellow-Green Group 146 C). Average Length. — About 5.0 mm to about 8.0 mm.

Flower buds:

*Hardiness*.—No winter injury (bud death) has been noted during the last several years of observation in the central San Joaquin Valley. The new variety of peach tree has not been intentionally subjected to drought, cold, or heat stress, and therefore this information is not available.

*Flower bud*.—Size — Variable, and dependent on the state of maturity. The flower buds as described were observed approximately 7 days prior to bloom. Length — About 14.5 mm. Diameter — About 10.0 mm. Surface Texture. — Pubescent. Orientation. — Considered appressed but appear less so as the blossoms near opening.

*Bud scale color*.—Approximately RHS Greyed-Orange Group 175 A.

Flowers:

*Date of first bloom*.—Observed on Feb. 27, 2022. Blooming Time. — Considered average to slightly early mid-bloom in relative comparison to other commercial peach cultivars grown in the central San Joaquin Valley. The date of full bloom was observed on Mar. 4, 2022. The date of full bloom varies slightly with climatic conditions and prevailing cultural practices. Duration of Bloom. — Approximately 9 or more days. This characteristic varies slightly with the prevailing climatic conditions.

*Flower class*.—Considered a perfect flower, complete and perigynous.

*Flower type*.—The variety is considered to have a showy type flower.

*Flower size*.—Considered large. The flower diameter at full bloom is about 46.0 mm to about 50.0 mm.

*Bloom quantity*.—Considered abundant.

*Flower bud density*.—Generally considered dense. Flower Bud Frequency. — Generally, two flower buds appear per node, while occasionally one flower bud per node is observed. Very rarely three floral buds per node are observed.

*Petal size*.—Generally considered medium for the species. Petal Length. — About 19.0 mm to about 22.0 mm. Petal Width. — About 16.0 mm to about 18.0 mm.

*Petal form*.—Considered broadly ovate.

*Petal count*.—Nearly always 5.

*Petal texture*.—Upper Petal Texture. — Very finely pubescent, satin like. Lower Petal Texture. — Very finely pubescent, satin like.

*Petal color*.—Considered a light pink at the popcorn stage (RHS Red-Purple Group 62 B).

*Fragrance*.—Slight.

*Petal claw*.—Form. — The claw is considered ovate and is generally large. Length. — About 12.0 mm. Width. — About 8.0 mm.

*Petal margins*.—Generally, slightly undulate.

*Petal apex*.—Apex margin appears entire.

*Flower pedicel*.—Length. — Considered medium with an approximate length of about 2.0 mm to about 3.0 mm. Diameter. — About 2.0 mm. Color. — A medium brown (approximately RHS Grey-Brown Group N199 D) depending on pedicel and fruit maturity and timing of visual observance. Strength. — Tenacious. Average for the species. Texture. — Generally smooth.

*Floral nectaries*.—Color. — Considered a burnt orange (approximately RHS Greyed-Orange Group N163 B).

*Calyx*.—Surface Texture. — Generally glabrous. Color. — Approximately RHS Greyed-Red Group 183 D.

*Sepals*.—Upper Surface Texture. — Moderately pubescent. Lower Surface Texture. — Finely pubescent. Number. — 5 sepals. Size. — Considered medium. Sepal Length. — About 4.0 mm to about 5.5 mm. Sepal Width. — About 3.5 mm to about 4.5 mm Sepal Shape. — Generally obovate. Sepal Margin. — Considered smooth and entire. Sepal Color. — Approximately RHS Greyed-Purple Group 187 B.

*Anthers*.—Generally. — Average in size. Color. — Yellow when viewed dorsally and just prior to dehiscence (approximately RHS Yellow-Orange Group 17 B). Position Relative to Stigma. — Generally, the stigma is superior to the anthers by about 1.0 mm to about 2.0 mm.

*Pollen production*.—Pollen is abundant and has a yellow color (approximately RHS Yellow-Orange Group 17 D).

*Fertility*.—Self-fertile.

*Filaments*.—Size. — About 12.0 mm to about 15.0 mm in length. Color. — Considered a light pink (RHS Red Group 55 B).

*Pistil*.—Number. — Usually one, and only rarely more than one. Generally. — Considered medium in size. Length. — About 14.0 mm to about 16.0 mm in length including the ovary. Color. — Considered a very pale green (approximately RHS Yellow-Green Group 145 D). Surface Texture. — The variety has a long pubescent pistil. Position Relative to Petals. — At flower maturity the stamens grow to be superior to the petals. Ovary. — Pubescent.

Fruit:

*Maturity when described*.—Firm ripe condition (shipping ripe).

*Date of first picking*.—Approximately Oct. 25, 2022.

*Date of last picking*.— Nov. 1, 2022. The date of harvest can vary with the prevailing climatic conditions. crop loads, and the current climatic and cultural practices.

*Size*.—Generally — Considered large.

*Average cheek diameter*.—About 84.0 mm to about 90.0 mm.

*Average axial diameter*.—About 83.0 mm to about 92.0 mm.

*Typical weight*.—About 335.0 grams. The fruit size and weight can vary and are dependent on the prevailing cultural practices and growing conditions and therefore is not particularly distinctive of the new variety.

*Fruit soluble solids*.—Approximately 15.0 to 18.0 Brix. Fruit sugar levels can vary significantly depending on fruit maturity, local and seasonal climatic conditions, fruit per tree.

*Fruit firmness*.—Fruit flesh pressures generally averaged 12.0 pounds at the time the fruit was analyzed.

*Titratable acidity*.—About 0.63 to about 0.73 at commercial harvest maturity.

*Fruit form*.—Generally — Considered globose. The fruit is generally very uniform in symmetry.

*Mucron tip*.—Can occasionally be observed.

*Fruit suture*.—No stitching exists along the suture line.

*Suture*.—Color — Generally, the fruit appears blushed to the same degree as the skin (approximately RHS Red Group 46 B).

*Ventral surface*.—Form — Considered even and uniform in appearance when it is viewed from the lateral, sutural plane.

*Apex*.—Shape — Generally rounded with occasional mucron tip.

*Base*.—Shape — Generally smooth.

*Stem cavity*.—Generally — It extends in a rounded circular form which is generally considered uniform. The stem cavity is rounded but slightly extended toward the suture. The average depth of the stern cavity is about 9.5 mm to about 13.0 mm. The average width of the stem cavity is about 29.0 mm. The average length of the stem cavity when measured in the sutural plane is about 40.0 mm.

*Fruit skin*.—Thickness. — Considered medium in thickness, and tenacious to the flesh. Surface Texture. — Pubescent. Taste. — Non-astringent. Tendency to crack. — Not observed in the previous years of observation and evaluation. Density of Pubescence. — Very sparse.

*Fruit skin color*.—Blush Color. — Generally speaking, a red blush exists on much of the skin of the fruit (approximately RHS Red Group 46 B) and is more typically present on the portions of the fruit facing the sunlight. The blush of the fruit typically covers approximately 45% to 60% of the fruit skin surface. The percentage of the blush on the fruit skin surface can vary and is generally dependent upon the fruit's exposure to direct sunlight, specific fruit maturity, and the prevailing ecological and cultural conditions under which the fruit was grown. The fruit blush pattern is considered mottled.

*Ground color*.—A medium yellow (approximately RHS Yellow-Orange Group 17 C). The ground color of the fruit can vary significantly based upon the maturity of the fruit when this measurement is taken and generally gains a lighter and less green cast with higher maturity.

*Fruit glossiness*.—Fruit is not considered to be glossy.

*Fruit stem*.—Size. — Medium in length, about 7.5 mm to about 9.5 mm. Diameter. — About 2.0 mm to about 3.0 mm. Color. — Pale yellow green (approximately RHS Yellow-Green Group 148 B).

*Fruit flesh*.—Ripening. — Considered even. Texture. — Firm, juicy, and dense. Considered non-melting in flesh classification. Fibers. — Present but not prominent. Aroma. — Present. Eating Quality. — Considered very good. Flavor. — Considered balanced with sweetness and acidity. Juice Production. — Moderate. Brix. — About 15.0 degrees to about 18.0 degrees. Acidity. — Considered medium. About 0.63 titratable acidity at fruit harvest. Acid levels assayed from fruit flesh can vary with fruit maturity; length of time in cold storage; sunlight exposure; and climatic, regional, seasonal, and cultural influences. Flesh Color. — It is considered yellow (approximately RHS Yellow-Orange Group 21 C). The present variety often exhibits red bleed, which radiates from about 4.0 mm to about 12.0 mm from the stone. Approximately RHS Red Group 45 B.

*Anthocyanin colorization*.—The intensity of the anthocyanin colorization of the flesh immediately beneath the skin surface is considered medium. and weak towards the central part of the flesh around the stone.

Stone:

*Type*.—Considered a clingstone.

*Size*.—It is generally considered to be medium for the species. The stone size varies significantly depending upon the tree vigor, the crop load. and the prevailing growing and cultural conditions under which the tree was grown.

*Length*.—Average, about 37.5 mm.

*Width*.—Average, about 30.0 mm.

*Diameter*.—Average, about 25.0 mm.

*Form*.—Roughly ovoid.

*Stone base*.—Shape — The stone is considered shortly attenuate.

*Apex*.—Shape — The stone exhibits a slight acute apex.

*Stone surface*.—Surface Texture — Considered furrowed toward the dorsal margin. Ridges. — Ridging is generally more prominent and is usually oriented parallel and laterally relative at the ventral and dorsal margins. Ventral Edge. — The ventral edge generally is described as having adjoining ridges formed from each hemisphere. There are longitudinal grooves running alongside this joined ventral suture. Dorsal Edge. — Shape — Generally considered even. The folds of the surface ridges appearing on the external margins often end gently along the suture.

*Stone color*.—The color of a mature, dry stone is generally considered a dull brown (approximately RHS Greyed-Orange Group 165 A). Stone color can vary considering how recently the fruit has ripened or harvested, the degree of oxidation, surface drying. and blanching due to exposure sunlight.

*Tendency to split*.—Splitting has rarely been noted.

*Kernel*.—Length. — About 14.0 mm to about 16.0 mm. Width. — About 10.0 mm to about 12.0 mm. Thickness. — About 5.0 mm to about 6.0 mm. Size. — The kernel is considered medium in size. Form. — Considered generally ovoid. Kernel Surface Texture. — Kernel pellicle is shortly pubescent. Color. — A dark tan (RHS Greyed-Orange Group N167 B).

*Use*.—The present variety 'Wapeachthree' is a peach tree of the late season of maturity, and which produces fruit which are considered to be firm, attractively colored, and which are useful for both local and long-distance shipping.

*Keeping quality*.—Appears excellent. The fruit of the present variety has stored well for periods of up to 25 days after harvest at 1.0 degree Celsius.

*Shipping quality*.—Good. The fruit of the new peach tree variety showed minimal bruising of the flesh or skin damage after being subjected to normal harvesting and packing procedures.

*Time of beginning of leaf bud burst*.—First enfoliation appears on approximately March 12.

*Resistance to insects and disease*.—No susceptibilities were noted. The present variety has not been intentionally tested to expose or detect any susceptibilities or resistances to any known plant or fruit diseases, insects, frost, winter injury, or other environmental factors.

Although the new variety of peach tree possesses the described characteristics when grown under the ecological conditions prevailing near Fowler, Calif., in the Central part of the San Joaquin Valley of California, variations of the usual magnitude and characteristics incident to changes in growing conditions. fertilization, nutrition, pruning, pest control, frost, climatic variables. and changes in horticultural management are to be expected.

Having thus described and illustrated our new variety of peach tree, what we claim is new, and desire to secure by plant Letters Patent is:

1. A new distinct variety of peach tree named 'Wapeachthree' substantially as illustrated and described, and which is characterized principally as to novelty by producing an attractively colored yellow-fleshed, clingstone peach which is mature for harvesting and shipment approximately October 25 to November 1 under the ecological conditions prevailing in the San Joaquin Valley of central California.

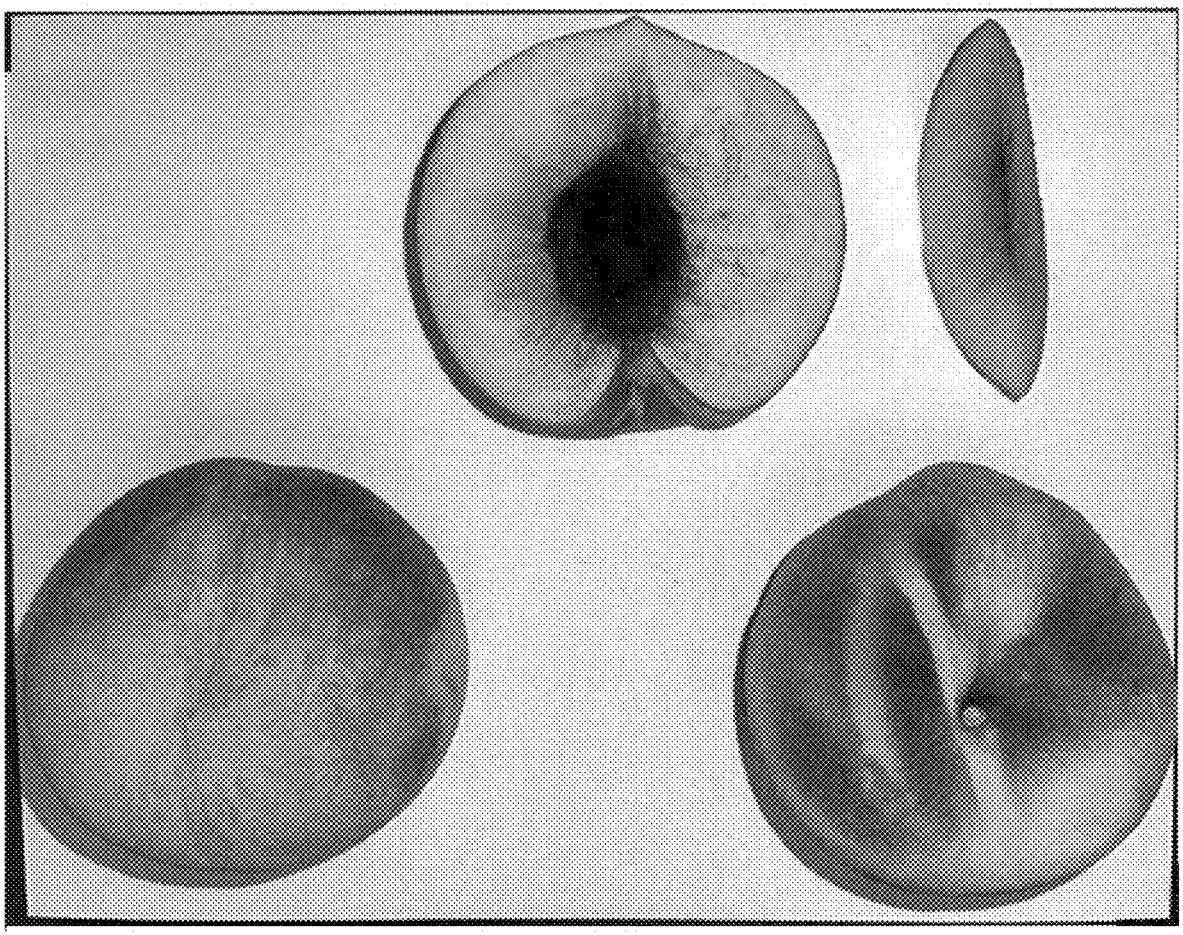

* * * * *